United States Patent
Lienhard et al.

(10) Patent No.: US 6,521,772 B1
(45) Date of Patent: Feb. 18, 2003

(54) SYNTHESIS OF SUBSTITUTED RUTHENOCENE COMPLEXES

(75) Inventors: Michael Alexander Lienhard, Buffalo, NY (US); Cynthia A. Hoover, Grand Island, NY (US); Jim D Atwood, Amherst, NY (US); David C. Hoth, East Aurora, NY (US)

(73) Assignees: Praxair Technology, Inc., Danbury, CT (US); Research Foundation of Suny, Buffalo, NY (US)

( * ) Notice: Subject to any disclaimer, the term of this patent is extended or adjusted under 35 U.S.C. 154(b) by 0 days.

(21) Appl. No.: 09/963,451

(22) Filed: Sep. 27, 2001

(51) Int. Cl.$^7$ .......................... C07F 17/02; C23C 16/18
(52) U.S. Cl. ................... 556/136; 427/252; 427/255.28
(58) Field of Search .................. 556/136; 427/252, 427/255.28

(56) References Cited

U.S. PATENT DOCUMENTS

| | | | | |
|---|---|---|---|---|
| 6,207,232 B1 | * | 3/2001 | Kadokura | .................. 427/252 |
| 6,420,582 B1 | * | 7/2002 | Okamoto | .................... 556/136 |
| 2001/0056198 A1 | * | 12/2001 | Kitada | ........................ 556/136 |
| 2002/0058106 A1 | * | 5/2002 | Okamoto et al. | ........... 427/250 |
| 2002/0064948 A1 | * | 5/2002 | Saito et al. | ................. 438/681 |
| 2002/0065427 A1 | * | 5/2002 | Okamoto | .................... 556/136 |
| 2002/0103395 A1 | * | 8/2002 | Saito | ........................... 556/136 |

FOREIGN PATENT DOCUMENTS

JP   2002-220397   *   9/2002

* cited by examiner

Primary Examiner—Porfirio Nazario-Gonzalez
(74) Attorney, Agent, or Firm—Robert J. Follett

(57) ABSTRACT

This invention is directed to a method for producing an alkyl-substituted metallocene complex comprising the steps of mixing a metallocene with a solvent to form a metallocene-solvent mixture; mixing the metallocene-solvent mixture with an effective amount of a metallation reagent to produce a metallated-metallocene; and mixing said metallated-metallocene with an electrophilic alkyl-reagent to form an alkyl-substituted metallocene complex.

15 Claims, No Drawings

SYNTHESIS OF SUBSTITUTED RUTHENOCENE COMPLEXES

FIELD OF THE INVENTION

This invention is related to a method of synthesizing organometallic materials. More specifically, this invention is directed to the synthesis of substituted ruthenocene complexes.

BACKGROUND OF THE INVENTION

Ruthenium (Ru) and ruthenium oxide ($RuO_2$) are materials that may be used as electrodes in future semiconductor devices (e.g. DRAM and Logic chips). These materials possess attractive physical properties, such as low electrical resistance, high work functions, inter-layer chemical diffusion resistance and thermal and oxidative stability. In addition, Ru and $RuO_2$ thin films have lattice parameters and thermal expansion coefficients that are compatible with many dielectric materials under consideration for future semiconductor devices.

Chemical vapor deposition (CVD) is a technique that is widely utilized in the fabrication of semiconductor devices to produce the layers of materials that make the devices. In CVD, chemical compounds (referred to as precursors) are transported in the vapor phase to or near a surface where they decompose by some means (e.g. thermal, chemical or plasma activation) to produce a solid film of a desired material composition. The use of CVD techniques to produce both ruthenium and ruthenium oxide thin films for semiconductor devices is known. See, WO 00/12766. Ruthenium compounds suitable for use as CVD precursors to ruthenium and ruthenium oxide thin films will be required if these materials are incorporated into commercial semiconductor devices using the CVD technique.

One class of compounds that appears to have suitable derivatives for CVD precursors are substituted cyclopentadienyl ruthenium complexes (SCRs) of the general formula $(C_5H_4R)Ru(C_5H_4R')$ [R,R'=H, alkyl, silyl, etc.]. Selected derivatives of this class of compounds meet several criteria desirable for their use as CVD precursors. They exist as liquids in the pure state at or near room temperature, possess moderate volatility, air stability, and most importantly have been demonstrated to produce Ru and $RuO_2$ films under appropriate CVD conditions. For example, the liquid derivative bis(ethylcyclopentadienyl) ruthenium has been reported to be a suitable CVD precursor for deposition of both Ru and $RuO_2$ films (See, e.g., Kim et. al., J. Electrochem Soc., 2000, 147 (3), pp. 1161–1167).

U.S. Pat. No. 6,002,036 discloses a method for the synthesis of a subclass of the substituted cyclopentadienyl ruthenium complexes, specifically bis (ethylcyclopentadienyl) ruthenium and bis (isopropylcyclopentadienyl) ruthenium (R $=CH_2CH_3$, $CH(CH_3)_2$ respectively). These compounds are reported to be liquids of moderate volatility at 25° C., which make them potentially attractive as $Ru/RuO_2$ CVD precursors. The '036 patent discloses a one step synthesis to produce bis (ethylcyclopentadienyl) ruthenium from ruthenium trichloride hydrate in 70% yield). This report is reasonably substantiated by an earlier report in the chemical literature for producing bis(cyclopentadienyl) ruthenium, (a ruthenocene) (R=H) using near identical reaction conditions (See, Pertici, P., Inorg. Synth., 1983, 22, p. 180). In these reactions ruthenium trichloride hydrate is reacted with cyclopentadiene or a substituted-cyclopentadiene and a reducing agent (such as zinc) in the presence of a solvent (such as alcohol) to produce SCRs.

Several alternate synthetic routes to alkyl-substituted cyclopentadienyl ruthenium compounds employing ruthenocene as a starting material are known. The production of monoethylcyclopentadienyl ruthenium (R=$CH_2CH_3$, R'=H) through a multi-step reaction sequence has been disclosed (See, Rausch, M. et al., J. Org. Chem., 1964, 3, 7 pp. 1067–1069). In this synthesis Friedel-Crafts acylation is employed to produce an acetyl substituted cyclopentadienyl ruthenium complex. The acyl group is then reduced to an alkyl group by using lithium aluminum hydride.

The use of Li-TMEDA to prepare metallated intermediates for nucleophilic substitution reactions has previously been reported for production of iodine substituted ruthenocene derivatives (See, Neuse E., J. Organomet. Chem., 1979, 168 p. C8–C12).

Finally, ruthenocene and bis(ethylcyclopenta-dienyl) ruthenium have also been prepared by the ligand exchange reaction between ruthenium trichloride and ferrocene or bis(ethylcyclopentadienyl) iron respectively in low yield. (See, Gauthier, G. J. Chem Soc. D, 1969 p. 690).

In order to successfully incorporate ruthenium CVD precursors into mainstream semiconductor fabrication processes, a suitable industrial process for their manufacture must be developed. The process must repeatedly produce material that meets the semiconductor industry's purity specifications. Due to the high cost of ruthenium (a platinum group metal) development of a high yield, low cost process is required to competitively produce these materials.

Kadokura disclosed that it produced bis (ethylcyclopentadienyl) ruthenium in a single step from ruthenium trichloride hydrate with a yield of 70%. To produce bis(ethylcyclopentadienyl) ruthenium using the invention described herein starting from ruthenium chloride, a two step synthesis is employed with an overall yield of at least about 65%. While the overall yield of the present invention is lower, it has several advantages. The most important advantage is that the present synthetic procedure permits the production of a greater variety of chemical derivatives; both mono-, bis- and tri-substituted products can be obtained by varying the stoichiometric amount of reactants employed. This is an advantage because the structure of the precursor effects its physical properties. Mono-substituted ruthenocene derivatives are expected to be desirably more volatile than similar bis-substituted compounds. In low-pressure CVD processes the surface chemistry ultimately determines film properties. For example, the sticking coefficient and surface lifetimes of the precursors will determine the process efficiency, while the surface mobility will effect the conformality of the deposited material. Thus, having a synthetic platform that provides access to a variety of similar derivatives is preferential to allow a comparative determination of which precursor structures lead to the desired film characteristics.

Additionally, the reagents employed in the invention reported here are commercially available, whereas the alkyl substituted cyclopentadienes are not. Thus, while the method of Kadokura can produce bis-alkyl substituted products in higher yield, an economic advantage is achieved only if the cost of the alkylcyclopentadiene is less than the cost of extra reagents used in this process. Again it should be stressed that Kadokura's method is clearly limited in its exclusive production of bis-substituted products.

The method disclosed by Rausch et. al. (Scheme 3) produces alkyl-substituted material starting from ruthenocene, uses commercially available reagents of similar cost to the invention described here, and is reported to produce alkyl-substituted ruthenocenes in similar yield. However, Rausch's route is not flexible since reduction chemistry on the acyl intermediate must be employed. Additionally the process steps are more labor intensive than those employed herein.

The ligand exchange process reported by Gauthier suffers the disadvantage of producing material in the poorest yield of all the processes discussed above. An additional disadvantage is the necessity of producing the alkyl-substituted cyclopentadienyl iron complex (and presumably employing one of the synthetic routes described here to do so) as a starting material. Finally iron is a key impurity in the final ruthenium products, so its inclusion in the synthetic route is not desirable.

The advantages of the present synthesis process includes the ability to synthesize a variety of different substituted cyclopentadienyl ruthenocene complexes in a manner that allows mono-, bis- or multiple substitution in a novel manner.

SUMMARY OF THE INVENTION

This invention is directed to a method for producing an alkyl-substituted metallocene complex comprising the steps of mixing a metallocene with a solvent to form a metallocene-solvent mixture; reacting the metallocene-solvent mixture with an effective amount of a metallation reagent to produce a metallated-metallocene; and mixing said metallated-metallocene with an electrophilic alkyl-reagent to form an alkyl-substituted metallocene complex.

The metallation reagent may be a Grignard reagent, trimethylsilyl potassium, organo-copper or an alkyl metallocene. The electrophilic alkyl-reagent is an alkyl silane or an alkyl halide. The solvent is less reactive than the metallation reagent, and may be cyclic ethers, linear ethers, crown ethers, polyethers, dioxanes and hydrocarbons, such as tetrahydrofuran, ethyl-ether and a mixture of tetrahydrofuran and ethyl-ether. The metallocene is ruthenocene.

As a preferred embodiment, this invention is directed to a method for producing substituted cyclopentadienyl ruthenocene complexes comprising reacting a ruthenocene with a solvent to form a ruthenocene-solvent mixture; reacting the ruthenocene-solvent mixture with an effective amount of alkyl-lithium reagent to form a alkyl-lithiated rutheonocene intermediate; and reacting the alkyl-lithiated ruthenocene intermediate with an electrophilic reagent to form a substituted cyclopentadienyl ruthenocene complex.

As used herein, a metallocene refers to a positively charged metal ion sandwiched between two negatively charged anions.

Further, as used herein, the word reacting refers generally to the process of combining, stirring, refluxing, heating, etc., and not necessarily resulting in a chemical reaction.

DETAILED DESCRIPTION OF THE INVENTION

The present invention provides an improved synthetic method for the production of substituted cyclopentadienyl ruthenium derivatives. Ruthenocene is reacted with an alkyl-lithium reagent to abstract proton(s) from the cyclopentadienyl ring(s) and form lithiated intermediate(s). After formation of the lithiated product is accomplished, it is essentially a nucleophile and reacts with an electrophilic reagent(s) (such as an alkyl halide), to produce SCRs. This is a 2-step reaction sequence. While both metallation and substitution of metallated species are known in the art in the general sense of chemistry, application of these routes to these compounds is novel.

In the broadest case, any metallation agent may be reacted with ruthenocene to produce any metallated ruthenocene. The degree of metallation (the number of protons removed and replaced with the metallation agent) is controlled by the stoichiometric addition of the reagent. The metallated agent is active to substitution reactions, and any suitable substituent may be added to produce a SCR.

As used herein, the starting material may be substituted ruthenocenes or any metallocene. Preferably, the starting material is alkyl substituted ruthenocenes, and more preferably, the starting material is ruthenocene.

The metallation reagent may be a Grignard Reagent, trimethylsilyl potassium, organo copper or any metallation reagent, preferably alkyl lithium, and more preferably, butyl lithium. Generally, the starting material may include $M(C_xH_yR_2)n$, wherein M is a D group metal, x=5–6, y=1–6, R=1–5 and n=2.

With respect to the stoichiometry, the ratio of metallation reagent to ruthenocene may be any amount, preferably a slight excess, and more preferably substantial excess of greater than about 50%.

The concentration of the reactant may comprise of any level of dissolution of starting materials or intermediates. Preferably, the concentration may be such that it is able to effect partial dissolution of starting material and intermediate. More preferably, the concentration is such that it is comprised of sufficient solvent to mostly dissolve starting material and almost entirely dissolve metallated intermediate.

The temperature of the reaction may be any temperature above the freezing point of the solvent to any temperature below the decomposition temperature of the solvents, starting material, or reactive intermediate. Preferably, the temperature is ambient ($\approx 25°$ C.) to reflux, depending on the solvent system, which in this case is 66° C. for THF.

As used herein, the reaction pressure in the present process is sub-atmospheric to high pressure. Preferably, the pressure is slightly above or below atmospheric pressure, and more preferably, at atmospheric pressure.

The electrophilic substituents may be any electrophilic reagent, preferably, an alkyl silane, and more preferably, an alkyl halide.

Of particular importance is the ability to produce both mono- or bis-substituted derivatives by varying the stoichiometry of the metallation reagent in the first synthetic step. By adding a large excess (>100%), the bis-substituted intermediate is primarily formed, whereas using a slight stoichiometric excess of metallation reagent the mono-substituted intermediate is formed. Using this process, either mono- or bis-substituted cyclopentadienyl derivatives may be formed. Three or more substituents may also be placed on the cyclopentadiene ring. Even though the di-substitution on the same ring may be small (when using a 300% excess RLi). The difficulty in di-substitution may be attributed to the proton becoming more basic as the carbon on the ring is metallated (i.e., after a proton is abstracted and the activity of an organo-lithium reagent is proportional to the acidity of the protons being removed.

Of additional importance, by using a mixture of reagents in the second synthetic step, di-substituted ruthenocene complexes where each R group is different (i.e. R and R' are not the same) may be generated.

Thus by using the synthetic process reported here, any of the following substituted cyclopentadienyl ruthenium complexes may be formed: mono-substituted (R=H, R'=electrophile), bis-substituted where R=R'=the same electrophile), and di-substituted where R and R' are different electrophiles.

The solvent should be chosen such that the ruthenocene is at least partially soluble (most preferably completely soluble) and the lithiated intermediate is at least partially soluble (most preferably completely soluble). The choice of an appropriate solvent and relative amount allows the 2-step process to be performed in a convenient one-pot reaction without having to change solvents, or isolate/purify the intermediates. The solvent used may be any solvent less reactive to the metallation reagent than the starting material, and preferably, cyclic ethers, linear ethers, crown ethers, polyethers, dioxanes, hydrocarbons, and more preferably, THF, ethyl-ether, or any mixture thereof.

EXAMPLE

Ruthenocene (5.5 g, 24 mMol) was transferred into a 250 ml 3-neck round bottom flask, equipped with a condenser, addition funnel and teflon stir bar. The apparatus was maintained under an inert atmosphere of nitrogen via a gas-cock atop the condenser. 50 ml of THF (freshly distilled from its blue solution with NA/benzophenone) was added to the flask, and the contents stirred. The dissolution of ruthenocene was observed to be incomplete, with the solution at 25° C. BuLi (15 mL of a 10M solution in hexane, 150 mMol, 300% excess) is pressure transferred into the addition funnel. The BuLi solution was added to the flask drop wise over a period of 1 hour. As the BuLi was added, the exothermic nature of the reaction causes the THF to undergo gentle reflux and allows all of the ruthenocene to dissolve. The solution was allowed to stir overnight, resulting in a yellow turbid solution. The solution is cooled to 0° C. in a water/ice bath. Ethyl bromide (17 g., 150 mMol, 300% excess) was pressure transferred to the addition funnel and introduced drop wise to the flask over a period of 1 hour. After addition was completed, the cooling bath was removed and the reaction mixture was allowed to warm to room temperature, with stirring for 2 hours. Toluene (100 mL) was added to the solution and the contents transferred to a 500 mL RB flask. This mixture was roto-evaporated under vacuum to remove the THF and allow the LiBr byproduct to precipitate from solution. The liquids were filtered through a 1 cm. thick layer of ceolite on top of filter paper, resulting in a clear yellow filtrate. The filtrate was roto-evaporated to remove the toluene yielding 6.2 g of yellow liquid. GC-MS analysis of the product revealed a 70% yield of bis (ethylcyclopentadienyl) ruthenium.

This invention provides for a versatile synthesis for producing mono-, bis-, or mixed substituted ruthenocene complexes. An improvement to herein was the use of a mixture of substituted cyclopentadienes (for example, cyclopentadiene and alkyl substituted cyclopentadiene) in the reaction. This improvement yielded a statistical mixture of hydrido, mono-alkyl and bis-alkyl products. However this would result in a lower overall yield of the desired product, to a yield comparable to the synthesis described herein. For example using Kadokura's method with a 1:1 ratio of EtCp and Cp would be expected to produce a 1:2:1 ratio of Cp$_2$Ru: (EtCp)Ru(Cp): (EtCp$_2$Ru).

If the desired product was (EtCp)Ru(Cp) the yield would therefore be about 50%.

It should be understood that the foregoing description is only illustrative of the invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for producing a substituted metallocene complex comprising
   a. mixing a metallocene with a solvent to form a metallocene-solvent mixture;
   b. mixing said metallocene-solvent mixture with an effective amount of a metallation reagent to produce a metallated-metallocene;
   c. mixing said metallated-metallocene with an electrophilic reagent to form a substituted metallocene complex.

2. The method of claim 1 comprising mixing said metallocene-solvent with a metallation reagent selected from the group consisting of Grignard reagent, trialkylsilyl salt, organo-copper and alkyl salt.

3. The method of claim 2 wherein said metallation reagent is Grignard reagent.

4. The method of claim 2 wherein said metallation reagent is butyl lithium.

5. The method of claim 1 wherein said electrophilic alkyl-reagent is an alkyl silane.

6. The method of claim 1 wherein said electrophilic alkyl-reagent is an alkyl halide.

7. The method of claim 1 comprising mixing a metallocene with a solvent selected from the group consisting of cyclic ethers, linear ethers, crown ethers, polyethers, dioxanes and hydrocarbons.

8. The method of claim 2 wherein said solvent is selected from the group consisting of tetrahydrofuran, ethyl-ether and a mixture of tetrahydrofuran and ethyl-ether.

9. The method of claim 1 wherein said substituted metallocene is selected from the group consisting of 5–8 member aliphatic rings, aromatic rings, and heterocyclic rings.

10. The method f claim 1 wherein said metallocene is ruthenccene.

11. A method of producing substituted cyclopentadienyl ruthenocene complexes comprising
    a. mixing a ruthenocene with a solvent to form a ruthenocene-so vent mixture;
    b. mixing said ruthenocene-solvent mixture with an effective amount of alkyl-lithium reagent to form a alkyl-lithiate rutheonocene intermediate;
    c. mixing said alkyl-lithiated ruthenocene intermediate with an lectrophilic reagent to form a substituted cyclopent dienyl ruthenocene complex.

12. The method of claim 11 wherein said alkyl-lithium reagent is a Crignard reagent.

13. The method of claim 11 wherein said electrophilic alkyl-re agent is an alkyl halide.

14. The method of claim 11 wherein said solvent is selected from the group consisting of cyclic ethers, linear ethers, crown Ethers, polyethers, dioxanes and hydrocarbons.

15. The method of claim 11 wherein said solvent is selected from the group consisting of tetrahydrofuran, ethyl-ether and a mixture of tetrahydrofuran and et ethyl-ether.

* * * * *

UNITED STATES PATENT AND TRADEMARK OFFICE
CERTIFICATE OF CORRECTION

PATENT NO.    : 6,521,772 B1
DATED         : February 18, 2003
INVENTOR(S)   : Lienhard et al.

It is certified that error appears in the above-identified patent and that said Letters Patent is hereby corrected as shown below:

<u>Column 6,</u>
Line 64, change "et ethyl-ether" to -- ethyl-ether --

Signed and Sealed this

Eighth Day of April, 2003

JAMES E. ROGAN
*Director of the United States Patent and Trademark Office*